(12) United States Patent
DeCoster et al.

(10) Patent No.: US 6,417,128 B1
(45) Date of Patent: Jul. 9, 2002

(54) METHODS AND REPLACING WATER AND CYCLOHEXANONE WITH ACETIC ACID IN AQUEOUS SOLUTIONS OF CATALYST

(75) Inventors: David C. DeCoster, Barrington, RI (US); Mark W. Dassel, Indianola, WA (US); Eustathios Vassiliou, Newark, DE (US); Ader M. Rostami; Douglas J. Dudgeon, both of Bainbridge Island, WA (US)

(73) Assignee: RPC, Inc., Atlanta, GA (US)

( * ) Notice: Subject to any disclaimer, the term of this patent is extended or adjusted under 35 U.S.C. 154(b) by 0 days.

(21) Appl. No.: 09/551,938

(22) Filed: Apr. 19, 2000

Related U.S. Application Data
(60) Provisional application No. 60/130,188, filed on Apr. 20, 1999.

(51) Int. Cl.[7] .......................... B01J 20/34; B01J 38/62; C07C 51/44; C07C 51/42; B01D 11/00
(52) U.S. Cl. .......................... 502/28; 203/16; 203/43; 203/47; 502/27; 502/29; 562/593; 562/590; 562/608
(58) Field of Search ............... 502/27, 28, 29; 203/16, 43, 47; 562/593, 590, 608

(56) References Cited

U.S. PATENT DOCUMENTS

| | | | |
|---|---|---|---|
| 1,121,532 A | 12/1914 | Newberry | 23/299 |
| 1,867,933 A | 7/1932 | Wilton | 261/111 |
| 2,014,044 A | 9/1935 | Haswell | 75/17 |
| 2,223,493 A | 12/1940 | Loder | 260/537 |
| 2,223,494 A | 12/1940 | Loder et al. | 260/586 |
| 2,301,240 A | 11/1942 | Baumann et al. | 183/115 |
| 2,439,513 A | 4/1948 | Hamblet et al. | 260/533 |
| 2,557,282 A | 6/1951 | Hamblet et al. | 260/533 |

(List continued on next page.)

FOREIGN PATENT DOCUMENTS

| | | |
|---|---|---|
| DE | 2 309 423 | 8/1974 |
| DE | 4426132 A1 | 1/1996 |
| DE | 4427474 A1 | 2/1996 |
| EP | 439 007 A2 | 7/1991 |
| EP | 494 416 A2 | 7/1992 |
| EP | 729 084 A1 | 8/1996 |
| EP | 729 085 A1 | 8/1996 |
| EP | 751 105 A2 | 1/1997 |

(List continued on next page.)

OTHER PUBLICATIONS

E. Sorribes et al., "Formación de nuevas fases en el proceso de obtención de ácido adípico: causas y efectos que provocan," *Rev. R. Acad. Cienc. Exactas, Fis. Nat. Madrid* (1987), 81 (1), 233–5 (+ English language translation).

Lewis, *Hawley's Condensed Chemical Dictionary*, 12th ed., 1993, pp. 7, 336, and 1076.

*Primary Examiner*—Steven P. Griffin
*Assistant Examiner*—Jonas N. Strickland
(74) *Attorney, Agent, or Firm*—Seed Intellectual Property Law Group PLLC

(57) ABSTRACT

This invention relates to methods of replacing water and cyclohexanone with acetic acid in an aqueous solution of catalyst, preferably a cobalt compound. Such an aqueous solution is produced by extracting catalyst with water from a cyclohexanone/water solution of reaction products made by the direct oxidation of cyclohexane to adipic acid. The replacement of both water and cyclohexanone are conducted in a solvent exchange column, wherein acetic acid dissolves the catalyst, while water vapors force the cyclohexanone into a condenser, followed by a decanter wherein two liquid phases may be formed and separated; an upper liquid phase containing a majority of cyclohexanone and a lower liquid phase containing a majority of water. The cyclohexanone may be removed in a pretreatment zone, wherein also part of the water may be removed, before the concentrated catalyst extract enters the solvent exchange column.

32 Claims, 4 Drawing Sheets

U.S. PATENT DOCUMENTS

| | | | |
|---|---|---|---|
| 2,565,087 A | 8/1951 | Porter et al. | 260/631 |
| 2,980,523 A | 4/1961 | Dille et al. | 48/215 |
| 3,161,603 A | 12/1964 | Leyshon et al. | 252/413 |
| 3,231,608 A | 1/1966 | Kollar | 260/533 |
| 3,234,271 A | 2/1966 | Barker et al. | 260/531 |
| 3,290,369 A | 12/1966 | Bonfield et al. | 260/537 |
| 3,361,806 A | 1/1968 | Lidov | 260/531 |
| 3,386,810 A | 6/1968 | Burke, Jr. et al. | 23/285 |
| 3,390,174 A | 6/1968 | Schulz et al. | 260/533 |
| 3,475,392 A | 10/1969 | McCoy et al. | 260/83.7 |
| 3,492,283 A | 1/1970 | Miller | 260/94.9 |
| 3,515,751 A | 6/1970 | Oberster et al. | 260/533 |
| 3,522,018 A | 7/1970 | Bachmann et al. | 23/285 |
| 3,530,185 A | 9/1970 | Pugi | 260/586 |
| 3,564,051 A | 2/1971 | Haarer et al. | 260/531 |
| 3,607,091 A | 9/1971 | Boyd | 23/253 |
| 3,613,333 A | 10/1971 | Gardenier | 55/89 |
| 3,649,685 A | 3/1972 | Ishimoto et al. | 260/533 C |
| 3,677,696 A | 7/1972 | Bryk et al. | 23/2 |
| 3,786,096 A | 1/1974 | Konno | 260/537 R |
| 3,819,813 A | 6/1974 | Jones, Jr. et al. | 423/421 |
| 3,839,435 A | 10/1974 | Shigeyasu et al. | 260/524 R |
| 3,869,508 A | 3/1975 | Longley et al. | 260/531 R |
| 3,926,738 A | 12/1975 | Nyiri et al. | 195/127 |
| 3,928,005 A | 12/1975 | Laslo | 55/73 |
| 3,932,513 A | 1/1976 | Russell | 260/586 AB |
| 3,946,076 A | 3/1976 | Paasen et al. | 260/586 P |
| 3,957,876 A | 5/1976 | Rapoport et al. | 260/586 P |
| 3,987,100 A | 10/1976 | Barnette et al. | 260/586 P |
| 3,987,808 A | 10/1976 | Carbonell et al. | 137/3 |
| 4,025,498 A | 5/1977 | Buss et al. | 260/95 A |
| 4,032,569 A | 6/1977 | Onopchenko et al. | 260/533 C |
| 4,039,304 A | 8/1977 | Bechthold et al. | 55/10 |
| 4,055,600 A | 10/1977 | Langley et al. | 260/586 P |
| 4,065,527 A | 12/1977 | Graber | 261/79 A |
| 4,158,739 A | 6/1979 | Schulz | 562/543 |
| 4,160,108 A | 7/1979 | Shigeyasu et al. | 562/416 |
| 4,161,573 A | 7/1979 | Gunsher et al. | 526/64 |
| 4,200,617 A | 4/1980 | Levy | 422/198 |
| 4,263,453 A | 4/1981 | Schulz et al. | 562/543 |
| 4,269,805 A | 5/1981 | Schoengen et al. | 422/106 |
| 4,279,846 A | 7/1981 | Ishii et al. | 264/41 |
| 4,308,037 A | 12/1981 | Meissner et al. | 55/10 |
| 4,332,590 A | 6/1982 | Smith | 23/230 A |
| 4,361,965 A | 12/1982 | Goumondy et al. | 34/57 R |
| 4,370,304 A | 1/1983 | Hendriks et al. | 422/224 |
| 4,394,139 A | 7/1983 | Board | 55/20 |
| 4,419,184 A | 12/1983 | Backlund | 162/49 |
| 4,423,018 A | 12/1983 | Lester, Jr. et al. | 423/247 |
| 4,477,380 A | 10/1984 | Knips et al. | 260/385 |
| 4,543,399 A | 9/1985 | Jenkins, III et al. | 526/70 |
| 4,588,790 A | 5/1986 | Jenkins, III et al. | 526/70 |
| 4,603,220 A | 7/1986 | Feld | 562/416 |
| 4,902,827 A | 2/1990 | Steinmetz et al. | 562/543 |
| 4,989,452 A | 2/1991 | Toon et al. | 73/293 |
| 5,061,453 A | 10/1991 | Krippl et al. | 422/106 |
| 5,104,492 A | 4/1992 | King et al. | 203/15 |
| 5,117,007 A | 5/1992 | Taheri | 549/259 |
| 5,123,936 A | 6/1992 | Stone et al. | 55/8 |
| 5,139,753 A | 8/1992 | Hardison | 423/220 |
| 5,170,727 A | 12/1992 | Nielsen | 110/346 |
| 5,188,805 A | 2/1993 | Sabottke | 422/111 |
| 5,206,701 A | 4/1993 | Taylor et al. | 356/325 |
| 5,210,297 A | 5/1993 | Frank et al. | 562/593 |
| 5,221,800 A | 6/1993 | Park et al. | 562/543 |
| 5,244,603 A | 9/1993 | Davis | 261/87 |
| 5,259,996 A | 11/1993 | Morgan | 261/114.1 |
| 5,270,019 A | 12/1993 | Melton et al. | 422/234 |
| 5,271,904 A | 12/1993 | Esposito et al. | 422/105 |
| 5,286,458 A | 2/1994 | Yang et al. | 422/168 |
| 5,294,378 A | 3/1994 | Succi et al. | 261/130 |
| 5,312,567 A | 5/1994 | Kozma et al. | 261/87 |
| 5,321,157 A | 6/1994 | Kollar | 562/543 |
| 5,374,767 A | 12/1994 | Drinkard et al. | 560/193 |
| 5,396,850 A | 3/1995 | Conochie et al. | 110/346 |
| 5,399,750 A | 3/1995 | Brun et al. | 562/553 |
| 5,463,119 A | 10/1995 | Kollar | 562/543 |
| 5,502,245 A | 3/1996 | Dassel et al. | 562/413 |
| 5,502,247 A | 3/1996 | Bartos et al. | 562/486 |
| 5,505,920 A | 4/1996 | Kollar et al. | 423/246 |
| 5,516,423 A | 5/1996 | Conoby et al. | 210/85 |
| 5,547,905 A | 8/1996 | Kulsrestha et al. | 502/66 |
| 5,558,842 A | 9/1996 | Vassiliou et al. | 422/108 |
| 5,580,531 A | 12/1996 | Vassiliou et al. | 422/108 |
| 5,654,475 A | 8/1997 | Vassiliou et al. | 562/413 |
| 5,756,837 A | 5/1998 | Costantini et al. | 562/543 |
| 5,801,273 A | 9/1998 | Vassiliou et al. | 562/413 |
| 5,801,282 A | 9/1998 | Dassel et al. | 562/413 |
| 5,817,868 A | 10/1998 | Rostami et al. | 562/413 |
| 5,824,819 A | 10/1998 | Dassel et al. | 562/529 |
| 5,877,341 A | 3/1999 | Vassiliou et al. | 560/77 |
| 5,883,292 A | 3/1999 | Dassel et al. | 562/413 |
| 5,908,589 A | 6/1999 | DeCoster et al. | 264/37.18 |
| 5,922,908 A | 7/1999 | Dassel et al. | 562/543 |
| 5,929,277 A | 7/1999 | DeCoster et al. | 562/593 |
| 5,980,801 A | 11/1999 | Dassel et al. | 264/176.1 |
| 6,037,491 A | 3/2000 | Vassiliou et al. | 562/413 |
| 6,039,902 A | 3/2000 | Rostami et al. | 264/37.18 |

FOREIGN PATENT DOCUMENTS

| | | |
|---|---|---|
| FR | 2 722 783 A1 | 1/1996 |
| GB | 415172 | 8/1934 |
| GB | 738808 | 10/1955 |
| GB | 864106 | 3/1961 |
| GB | 1143213 | 2/1969 |
| GB | 2 014 473 A | 8/1979 |
| GB | 2 072 667 A | 10/1981 |
| JP | 48-003815 | 2/1973 |
| JP | 50034006 B | 11/1975 |
| JP | 54-33891 | 3/1979 |
| JP | 61 063634 | 4/1986 |
| WO | WO 94/07833 | 4/1994 |
| WO | WO 94/07834 | 4/1994 |
| WO | WO 96/03365 | 2/1996 |
| WO | WO 96/14288 | 5/1996 |
| WO | WO 96/40610 | 12/1996 |
| WO | WO 97/49485 | 12/1997 |
| WO | WO 99/14178 | 3/1999 |

METHODS AND REPLACING WATER AND CYCLOHEXANONE WITH ACETIC ACID IN AQUEOUS SOLUTIONS OF CATALYST

CROSS-REFERENCE TO RELATED APPLICATION

This application claims the benefit under 35 U.S.C. §119 (e) of U.S. Provisional Patent Application No. 60/130,188, filed Apr. 20, 1999.

FIELD OF THE INVENTION

This invention relates to methods of recycling catalyst, and more specifically it relates to methods of exchanging solvents in a solution of catalyst, produced after oxidation of cyclohexane to adipic acid, in a manner to render the catalyst beneficially recyclable to the beginning of the oxidation process.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic from the "Polar Phase" and recycling these phases to the reactor partially or totally with or without further treatment.

It is also important to note that most studies on the Direct Synthesis—have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by (1) reacting,
   (a) at least one saturated cycloaliphatic hydrocarbon having from 5 to 8 ring carbon atoms in the liquid phase and
   (b) an excess of oxygen gas or an oxygen-containing gas in the presence of
   (c) a solvent comprising an organic acid containing only primary and/or secondary hydrogen atoms and
   (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by (1) reacting, at a cycloaliphatic hydrocarbon conversion level of between about 7% and about 30%,
   (a) at least one saturated cycloaliphatic hydrocarbon having from 5 to 8 ring carbon atoms in the liquid phase and
   (b) an excess of oxygen gas or an oxygen containing gas mixture in the presence of less than 1.5 moles of a solvent per mole of cycloaliphatic hydrocarbon (a), wherein said solvent comprises an organic acid containing only primary and/or secondary hydrogen atoms and
   (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° C. to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Costantini et al.) and U.S. Pat. No. 5,756,837 (Costantini et al.) disclose a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

The patent literature is inconsistent and at least confusing regarding addition or removal of water in oxidations. For example:

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° C. and 160° C., while removing the water of reaction substantially as quickly as it is formed.

None of the above references, or any other references known to the inventors disclose, suggest or imply, singly or in combination, catalyst treatment for recycling subject to the intricate and critical controls and requirements of the instant invention as described and claimed.

Our U.S. Pat. Nos. 5,654,475, 5,580,531, 5,558,842, 5,502,245, 5,801,282, and co-pending application 08/587,967, filed on Jan. 17, 1996 (now U.S. Pat. No. 5,883,292, issued Mar. 16, 1999), all of which are incorporated herein by reference, describe methods and apparatuses relative to controlling reactions in atomized liquids. In addition, our U.S. Pat. Nos. 5,801,273 and 5,817,868, and the following co-pending U.S. applications are also incorporated herein by reference: 08/812,847, filed on Mar. 6, 1997; 08/824,992, filed on Mar. 27, 1997 (now U.S. Pat. No. 5,922,908, issued Jul. 13, 1999); 08/861,281 filed on May 21, 1997; 08/861,180 filed on May 21, 1997 (now allowed) 08/861,176 filed on May 21, 1997 (now U.S. Pat. No. 5,824,819, issued Oct. 20, 1998); 08/861,210 filed on May 21, 1997 (now abandoned); 08/876,692, filed on Jun. 16, 1997; 08/900,323, filed on Jul. 25, 1997 (now U.S. Pat. No. 6,037,491, issued Mar. 14, 200); 08/931,035, filed on Sep. 16, 1997 (now abandoned); 08/932,875 (now U.S. Pat. No. 6,039,902, issued Mar. 21, 2000) filed on Sep. 18, 1997; 08/934,253, filed on Sep. 19, 1997 (now U.S. Pat. No. 5,929,277, issued Jul. 27, 1999); 08/986,505 (now U.S. Pat. No. 5,908,589, issued Jun. 1, 1999), filed on Dec. 8, 1997; 08/989,910, filed on Dec. 12, 1997; 60/074,068, filed on Feb. 9, 1998; 60/075,257, filed Feb. 19, 1998; 60/086,159, filed May 20, 1998; 60/086,119, filed May 20, 1998; 60/086,118, filed May 20, 1998; 60/091,483, filed on Jul. 2, 1998; 60/091,796, filed Jul. 6, 1998; 60/093,256, filed Jul. 17, 1998; 60/105,048, filed Oct. 20, 1998; 60/101,918, filed on Nov. 24, 1998; 60/110,206, filed on Nov. 30, 1998; 60/111,848, filed Dec. 11, 1998; 60/121,170, filed Feb. 22, 1999; and 60/122,705, filed Mar. 3, 1999.

SUMMARY OF THE INVENTION

As aforementioned, this invention relates to methods of exchanging solvents in a solution of catalyst, produced after oxidation of cyclohexane to adipic acid, in a manner to render the catalyst beneficially recyclable to the beginning of the oxidation process. More specifically, this invention relates to a method of replacing water and cyclohexanone with acetic acid in an aqueous solution of a metal catalyst, the solution having been produced after oxidation of cyclohexane to adipic acid, the method comprising steps of:

(a) feeding the aqueous solution of the metal catalyst to a top plate or an intermediate plate of a solvent exchange column, the solvent exchange column also having a bottom plate;

(b) removing a bottoms liquid from the vicinity of the bottom plate, the bottoms liquid being at a bottoms temperature;

(c) boiling the bottoms liquid in a re-boiler and returning produced bottoms vapors to the column in the vicinity of the bottom plate:

(d) introducing acetic acid to the re-boiler; and (e) removing from the re-boiler an acetic acid solution of the metal catalyst comprising no substantial amounts of water and cyclohexanone.

The method of the instant invention may further comprise steps of removing top vapors from the vicinity of the top plate of the solvent exchange column, condensing said vapors to form a condensate, and, if the condensate constitutes two liquid phases, separating said condensate into an upper liquid phase comprising a majority of cyclohexanone, and a lower liquid phase comprising a majority of water.

Preferably, the metal catalyst comprises a cobalt compound.

In addition, the method may further comprise a step of adding water to either the re-boiler, or to the solvent exchange column, or to both.

The water content in the bottoms liquid may be controlled and maintained at a level higher than that under which metal catalyst precipitates at or over the bottoms temperature. The water content may be further controlled, preferably in a manner to still remain low enough to be suitable for recycling to a reaction chamber of the oxidation of cyclohexane to adipic acid without formation of a second liquid phase.

It is also preferable that the majority of the cyclohexanone and at least part of the water are removed before the catalyst extract enters the solvent exchange column.

A condensate formed on top of the solvent exchange column may be at least partially recycled to said exchange column.

The temperature of the column, including the bottoms temperature, may be controlled and lowered by reducing the pressure within the column by techniques well known to the art, such as use of vacuum pumps for example. The control of the temperature may be necessitated to prevent catalyst precipitation at the water levels prevailing at the vicinity of the bottom plate or the re-boiler loop.

The methods of the present invention may further comprise a step of reacting the adipic acid produced with a reactant selected from a group consisting of a polyol, a polyamine, and a polyamide in a manner to form a polymer of a polyester, or a polyamide, or a (polyimide and/or polyamideimide), respectively. These methods may also comprise a step of spinning the polymer into fibers or mixing the polymer with fillers and/or other additives to form composites.

"Major" and "majority" regarding a moiety mean more than 50%, and up to substantially 100%, of said moiety by weight.

"Minor" and "minority" regarding a moiety mean less than 50%, and down to 0%, of said moiety by weight.

"Intermediate plate" is any plate between the top plate and the bottom plate.

BRIEF DESCRIPTION OF THE DRAWINGS

The reader's understanding of this invention will be enhanced by reference to the following detailed description taken in combination with the drawing figure, wherein.

DETAILED DESCRIPTION OF THE INVENTION

Figure 1:
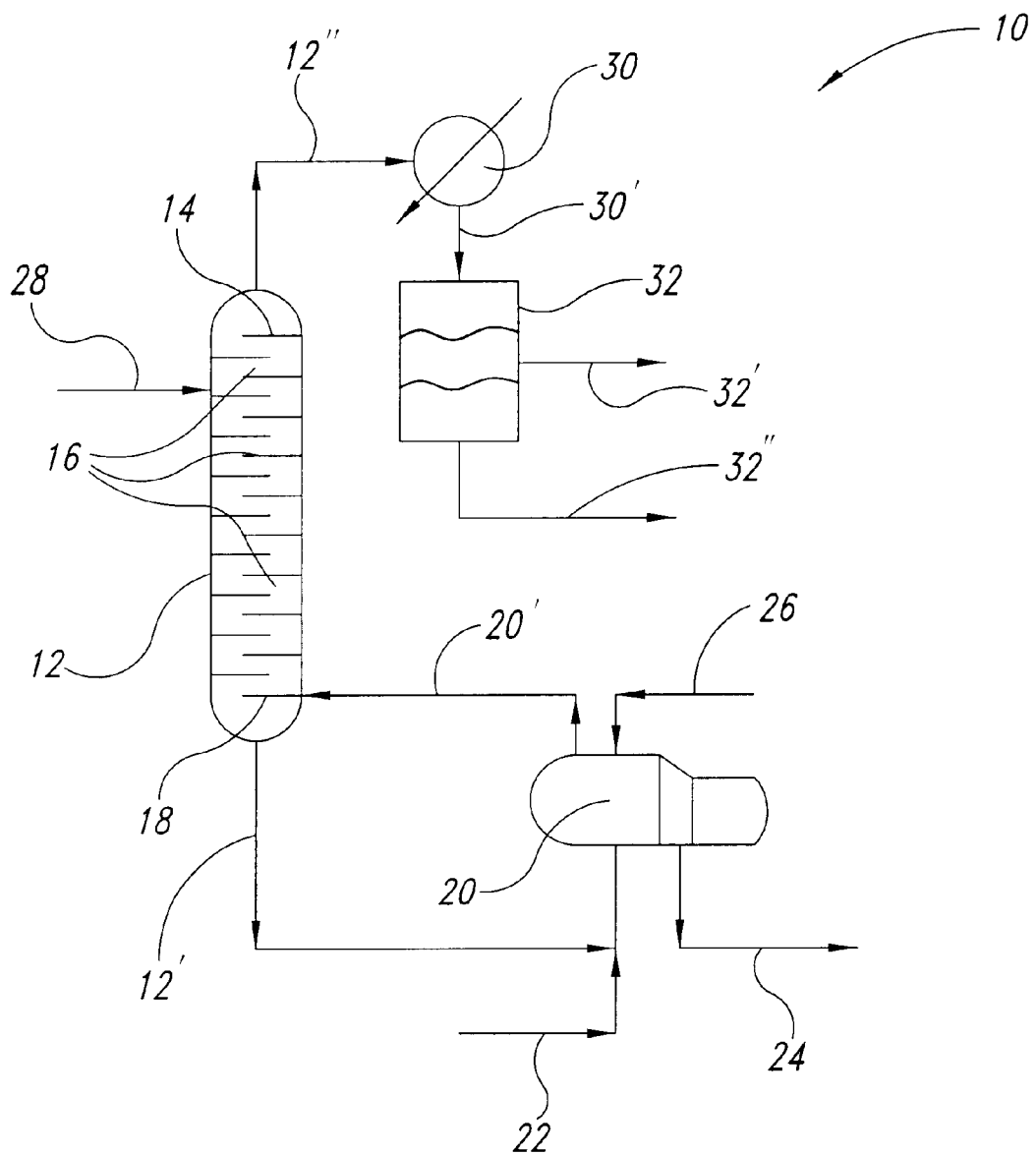
FIG. 1 illustrates a block diagram of a preferred embodiment of the present invention.

As aforementioned, this invention relates to methods of exchanging solvents in a solution of catalyst, produced after oxidation of cyclohexane to adipic acid, in a manner to render the catalyst beneficially recyclable to the beginning of the oxidation process.

Examples of catalyst solutions benefiting from the teachings of the instant invention are the catalyst extracts obtained according to the methods described in our patent applications 60/091,483, filed on Jul. 2, 1998; 60/091,796, filed Jul. 6, 1998; 60/093,256, filed Jul. 17, 1998; 60/105,048, filed Oct. 20, 1998; 60/101,918, filed on Nov. 24, 1998; 60/110,206, filed on Nov. 30, 1998; 60/111,848, filed Dec. 11, 1998; 60/121,170, filed Feb. 22, 1999; and 60/122,705, filed Mar. 3, 1999 all of which are incorporated herein by reference.

These extracts are aqueous solutions of metal catalyst, such as cobalt salts for example, with minor amounts of cyclohexanone, dibasic acids, such as for example adipic acid, glutaric acid, and succinic acid, esters, and other by-products of the direct oxidation of cyclohexane to adipic acid by oxygen.

The aqueous catalyst extracts cannot be recycled directly to the oxidation zone of cyclohexane to adipic acid because of the abundance of water present. The abundance of water that would enter the oxidation zone when recycling the total amount of catalyst in the extract would be high enough to cause two liquid phase formation in the reaction chamber, and thereby, unacceptable reduction of the reaction rate.

In addition to the above technical factor, caused by the abundance of water in the catalyst extract, there is also a serious economic factor due to the cyclohexanone present in the extract. Cyclohexanone is rather expensive, and although it is present only in a minor level in the catalyst extract, the loss of cyclohexanone through direct feeding the catalyst extract to the oxidation zone would be economically unacceptable.

One way to avoid the above adverse factors is to remove the water and the cyclohexanone by evaporation, and then transfer just the residue to the oxidation zone. Although such a process seems at first glance to be relatively easy, it introduces nevertheless a new unacceptable technical task. The residue remaining after evaporation of the water and the cyclohexanone is a tacky mass, which would deposit tenaciously on all parts of the device with which it would come in contact, it would clog pipes, valves, and heat transfer surfaces, and it would present insurmountable problems regarding its transfer from the evaporation zone to the oxidation zone. Even in the case that one would proceed with a step of dissolving the tacky mass in a solvent, such as acetic acid for example, the deposition and clogging problems would not be alleviated in the vicinity of the evaporation zone.

The inventors discovered unexpectedly that both water and cyclohexanone may be replaced by acetic acid without solids formation by using a simple solvent exchange column, as it will be explained in detail hereinbelow.

Referring now to FIG. 1, there is depicted a novel solvent exchange system 10 comprising a solvent exchange column 12. The solvent exchange column 12 has a top plate 14, intermediate plates 16, and a bottom plate 18. The solvent exchange column 12 is connected to a re-boiler 20 through liquids line 12', which liquids line 12' starts at the vicinity of the bottom plate 18, and merges with an acetic acid line 22 before entering the re-boiler 20.

The re-boiler 20 is in turn connected back to the solvent exchange column 12 in the vicinity of the bottom plate 18 through vapors line 20'. The re-boiler 20 is also connected to a catalyst exit line 24. An additives line 26 is also connected to the re-boiler 20.

An extract line 28 is shown to be connected to the vicinity of an intermediate plate 16, but it may also be connected to the vicinity of the top plate 14. Preferably, it is connected to the solvent exchange column 12 in the vicinity of an intermediate plate 16 closer to the top plate 14 than to the bottom plate 18.

The solvent exchange column 12 is connected to a condenser 30 through line 12", which line 12" starts in the vicinity of the top plate 14.

The condenser 30 is connected to a decanter 32 through line 30', which is in turn connected to a cyclohexanone exit line 32', and to a water exit line 32".

In operation of this embodiment, an aqueous solution or extract of catalyst comprising minor amounts of cyclohexanone, as compared to the water, is introduced to the solvent exchange column 12 through extract line 28. In the solvent exchange column 12, vapors of acetic acid move upward in a direction from the bottom plate 18 toward the top plate 14. As the acetic acid vapors move upward in the column, they condense and the water and cyclohexanone of the extract vaporize. The condensate moves downwards with dissolved catalyst, and the water and cyclohexanone vapors move upwards, ultimately being removed through line 12'.

Based on boiling points (approx. 156° C. for cyclohexanone, 118° C. for acetic acid, and 100° C. for water), one would expect the condensation of acetic acid and the removal of water in a column such as this, but one would also expect that the cyclohexanone, being by far the highest boiler of all three, and being totally soluble in acetic acid, would condense along with the acetic acid and would move downward in the solvent exchange column However, cyclohexanone efficiently separates from acetic acid as an azeotrope with water, and it leaves the solvent exchange column along with the water through line 12".

The water and cyclohexanone leaving the solvent exchange column 12, through line 12", enter the condenser 30, where they form a condensate, which is directed to the decanter 32 through line 30'. In the decanter 32, the condensate may form two liquid phases; an upper liquid phase containing a major amount of cyclohexanone, and a lower liquid phase containing a major amount of water. The upper liquid phase contains also minor amounts of water and possibly acetic acid, while the lower liquid phase contains minor amounts of cyclohexanone and acetic acid, although the amount of acetic acid overhead may be greatly reduced by reflux to the column. The upper phase is removed through line 32', while the lower phase is removed through line 32". No catalyst is transferred to the condenser 30.

As mentioned earlier, it is preferable that the extract line 28 leads to the vicinity of one of the intermediate plates, since less acetic acid will follow the path of line 12" by this arrangement than if the extract line 28 were connected to a region in the vicinity of the top plate 14. However, the extract line 28 connection should not be too low because the column would become inefficient. It should be closer to the top plate 14 than to the bottom plate 18.

The temperature in the vicinity of the top plate 14 and in the vicinity of the intermediate plates corresponding to the connection of extract line 28 to the solvent exchange column 12 is maintained preferably around 100° C. The temperature in the vicinity of the bottom plate 18 is preferably maintained in the range of 120°–125° C.

The condensed acetic acid in the solvent exchange column 12 is transferred through line 12' to the re-boiler 20, either directly (not shown) or after it has been merged with the acetic acid line 22. Of course, the acetic acid line 22 may be connected directly to the re-boiler 20, or the base of the column (not shown).

Acetic acid enters the re-boiler 20 through the acetic line 22. The flow rate of the acetic acid entering the re-boiler 20 through the acetic acid line 22 determines the dilution of the catalyst in a solution exiting the re-boiler 20 thorough line 24. The catalyst solution in acetic acid exiting the re-boiler 20 through line 24 contains all the catalyst which enters the column 12 through line 28, substantially no cyclohexanone, a very small amount of water (preferably on the order of 0.1 to 1%), and minor amounts of by-products which enter the solvent exchange column through line 28, such as dibasic acids, esters, etc. The solution in line 24 is suitable for recycling directly to the oxidation stage without any further treatment, although additional treatments may be applied if so desired.

Water may be added to the re-boiler 20 through the additives line 26 for controllably increasing the water content of the condensed liquids in the vicinity of the bottom plate 18. Of course, addition of water through the additives line 26 will also increase somewhat the water content of the solution exiting through line 24. The water content in the vicinity of the bottom plate 18 is kept higher than a water content at which or under which catalyst precipitates due to excessive dehydration of the cobalt catalyst at the unique combination of temperatures, ligand structures, catalyst concentrations, etc., prevailing in the vicinity of the bottom plate 18.

The dimensions of the column, the number of plates, the position at which the extract line 28 is connected to the solvent exchange column 12, the size of the re-boiler, the heat provided to the re-boiler, etc., depend on individual circumstances, and they can be determined very easily by a person of ordinary skill in the art without undue experimentation.

Thus, this system provides an excellent method of efficient solvent exchange without solids formation at any stage.

Figure 2:
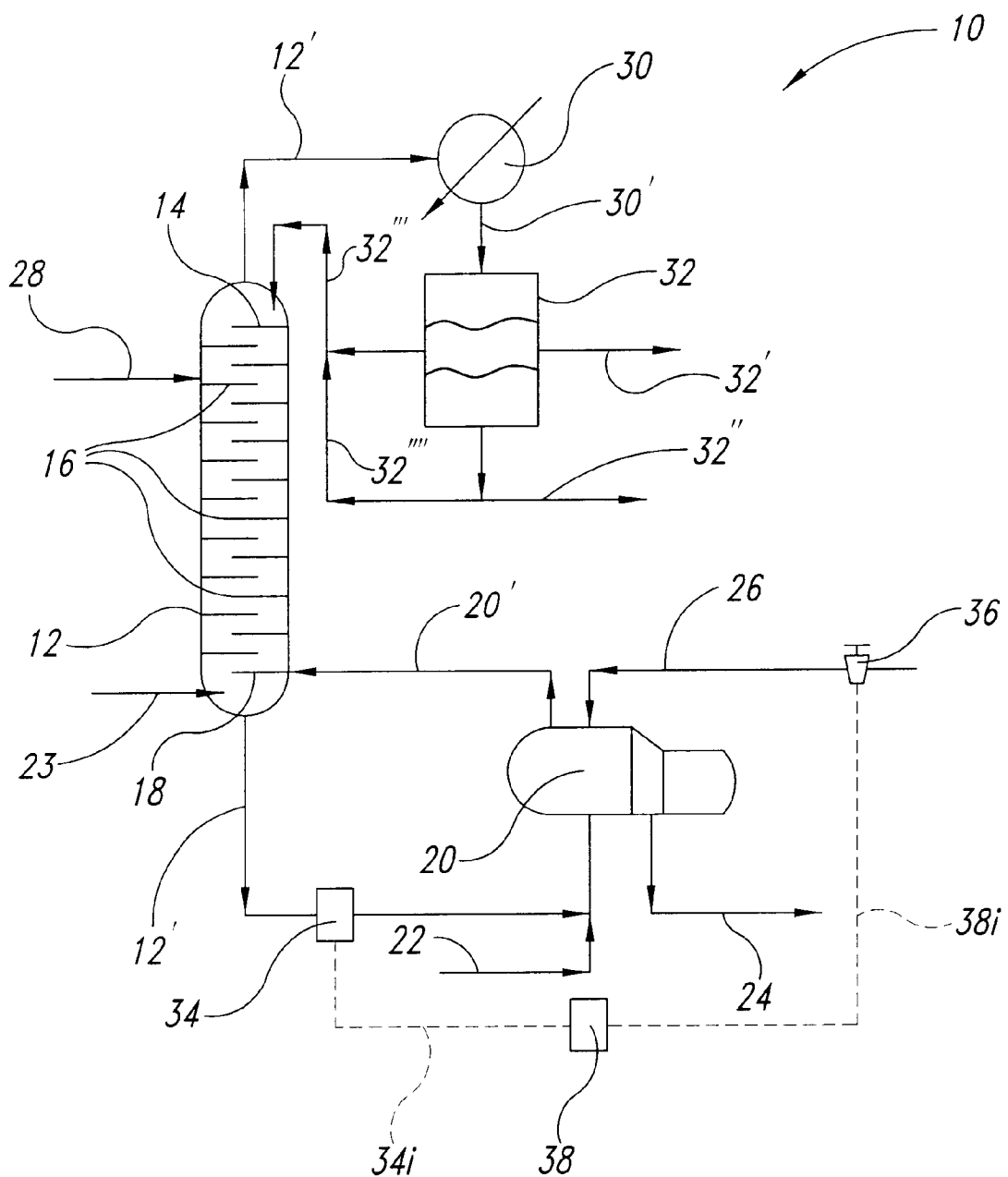
FIG. 2 illustrates a block diagram of another preferred embodiment of the present invention.

In another preferred embodiment, better illustrated in FIG. 2, a similar configuration to that of FIG. 1 is shown, which incorporates additional features.

A second acetic acid line 23 is connected in the vicinity of the bottom plate 18, through which acetic acid may be provided to the system during the operation. The second acetic acid line 23 may be in addition or it may replace the acetic acid line 22.

An on-line water analyzer 34 is connected to line 12', and to a controller 38 through line 34i. The controller 38 is in turn connected to and controls a valve 36, which is connected to additives line 26. The controller 38 may be an individual controller or part of a considerably more complicated controller (not shown) which controls the operation of the whole system. In operation, the water analyzer 34 analyzes the stream moving through line 12' and determines the water content in said stream. In turn it provides this information to the controller 38 through line 34i, which in turn increases or decreases the opening of the additives valve 36 in the range from a completely closed position to a completely open position.

The water content in the vicinity of the bottom plate 18 may also be regulated by the boil-up ratio, or other methods.

As aforementioned the water level in the vicinity of the bottom plate 18, and therefore in the stream of line 12', has to be within a predetermined level having an upper limit and a lower limit. If the water level is above the predetermined limit, it may cause formation of two liquid phases in the reaction chamber (not shown) to which the catalyst is going to be recycled. If the water level is lower than the lower limit, it may cause catalyst precipitation. This predetermined range of water levels depends on a number of factors, including the conditions in the reaction chamber (not shown) with regard to the upper limit, and temperature, the catalyst associated ligands, the catalyst concentration, and miscellaneous by-products concentrations, among others, with regard to catalyst precipitation. If the water level is below the predetermined lower limit, the controller 38 causes the control valve 36 to open incrementally until the water level falls again within the predetermined range. The opposite action is taken by the controller 38 and the control valve 36 if the water level exceeds the upper limit of the predetermined range.

Control of the temperature in the vicinity of the bottom plate 18 may be achieved by pressure control. The lower the pressure in the column, the lower the operational temperature. The lower the temperature, the lower the lower limit of the predetermined range.

It is believed that in the vicinity of the bottom plate 18, ligand exchange takes place to at least a certain degree, because of the excessive abundance of acetic acid. Thus, salts of cobalt with dibasic acids entering the column through extract line 28 are at least partially transformed to acetic acid salts with cobalt.

It is important to note that water level may be divided into two kinds; free water dissolved in acetic acid and crystalline water bound to the catalyst. Thus, catalyst may be prevented from precipitating even in cases in which the free water is 0%, and the crystalline water is even less than 4 moles of water per mole of cobalt atom (for example in one of our experiments, the mole ratio of water to cobalt was 1.7 to 1 without catalyst precipitation). Therefore, it is important that both the free and the crystalline water are monitored and controlled by techniques well known to the art. Thus, according to this invention, the free water level can be considerably lower than 0.3% without catalyst precipitation.

Lines 32''' and 32'''', which connect the decanter back to the vicinity of the top plate 14 of the column 12, may be utilized to reflux part of the cyclohexanone phase and part of the water phase, respectively. The reflux helps to reduce the amount of acetic acid entering the condenser 30 from the column 12 through line 12'. The reflux of the two liquid phases may be carried out in any appropriate proportions. Of course, in the case of existence of just one single liquid phase in the decanter 32, reflux of the single liquid phase may be performed. It is evident that in the case of just one single liquid phase condensate, there is no need of using a decanter.

The amount of acetic acid passing to the condenser 30 is preferably less than 10%, more preferably less than 5%, and even more preferably less than 1%. One reason for preferring substantial absence of acetic acid in the condensate is that the cyclohexanone stream through line 32' and the water stream through line 32'' are utilized in the catalyst extraction station as described in our U.S. patent applications Ser. No. 60/091,483, filed on Jul. 2, 1998; 60/091,796, filed Jul. 6, 1998; 60/093,256, filed Jul. 17, 1998; 60/105,048, filed Oct. 20, 1998; 60/101,918, filed on Nov. 24, 1998; 60/110,206, filed on Nov. 30, 1998; 60/111,848, filed Dec. 11, 1998; 60/121,170, filed Feb. 22, 1999; and 60/122,705, filed Mar. 3, 1999 all of which are incorporated herein by reference. We have found that the catalyst extraction with water is considerably more efficient in the substantial absence of acetic acid.

Even if no substantial amounts of acetic acid are introduced through line 28 in the above embodiments, the water leaving the solvent exchange system through line 32'' contains about 5–10% acetic acid by weight.

The catalyst solution in acetic acid leaving the system through line 24 may be controlled to contain about, if so desired, 0.5% or less free water in acetic acid by weight.

Figure 3:
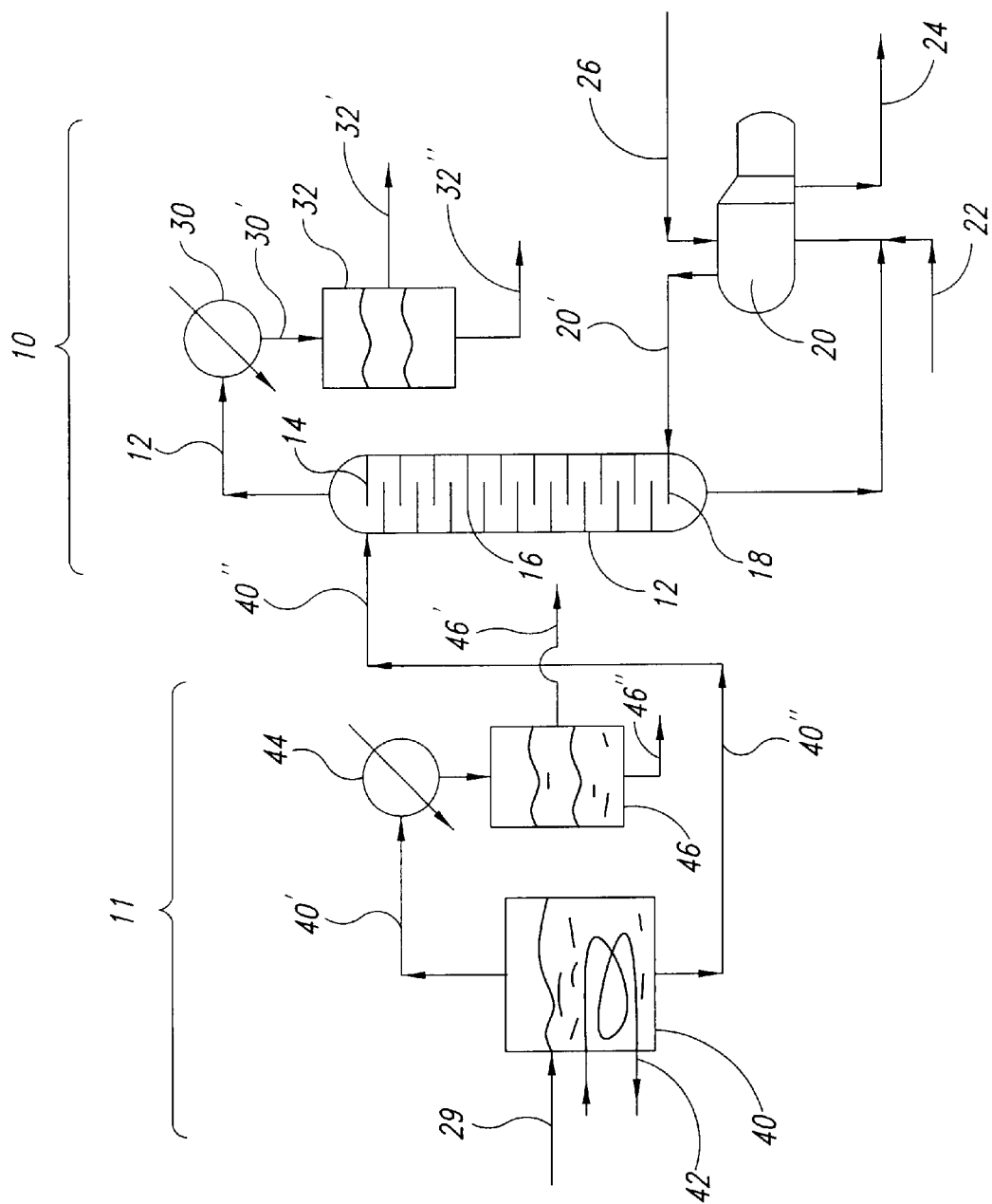
FIG. 3 illustrates a block diagram of still another preferred embodiment of the present invention, which incorporates a pre-flasher.

A considerably more efficient system is shown in FIG. 3, wherein the solvent exchange system 10 is preceded by a pretreatment station 11 comprising a pre-flasher 40, which is heated by a coil (for example a steam operated coil) 42. The pre-flasher 40 is connected to a second condenser 44, which is in turn connected to a second decanter 46. The second decanter 46 is connected to a second cyclohexanone exit line 46' and to a second water exit line 46''. The pre-flasher 40 is connected to the vicinity of the top plate 14 of the solvent exchange column 12. A second extract line 29 is also connected to the pre-flasher 40.

In operation of this embodiment, catalyst extract, as described in the previous embodiments, enters the pre-flasher 40 through the second extract line 29. The catalyst extract contains an aqueous solution of cobalt salts, as well as cyclohexanone. As aforementioned, the catalyst extract, preferably, does not contain any substantial amounts of acetic acid. The conditions are preferably maintained such that most of the cyclohexanone and a large amount of water (about ⅔ of the water for example) are removed (at least partially as an azeotrope) through line 40', they are condensed in the second condenser 44, and then they are decanted in the second decanter 46 into an upper liquid phase containing mainly cyclohexanone, and a lower liquid phase containing mainly water. The upper liquid phase is recycled through the cyclohexanone exit line 46', and the lower liquid phase is recycled through the water exit line 46" to the catalyst extraction system (not shown) described in the patent applications mentioned earlier.

The concentrated aqueous extract is in turn introduced to the vicinity of the top plate 14 of the column 12 through line 40". The operation from this point on is substantially the same as in the previous cases.

Since in this case it is preferable to remove almost all the cyclohexanone and collect it in the second decanter 46, the amount of cyclohexanone condensed in the condenser 30 and introduced in the decanter 32 is very little, and in most cases a single liquid phase will be present. In such cases of one single liquid phase, the decanter is obviously not necessary. The amount of the acetic acid in the decanter, regardless of whether there is one or two liquid phases, will be much less than in the previous embodiments, and closer to about 1% by weight.

Again, the catalyst solution in acetic acid leaving the system through line 24 may be controlled to contain about, if so desired, 0.5% or less free water in acetic acid by weight.

If there is some acetic acid in the second extract line 29, it is preferable that line 40" is connected to the vicinity of an intermediate plate 16, thus forming an upper rectification section in addition to a lower stripping section.

Figure 4:
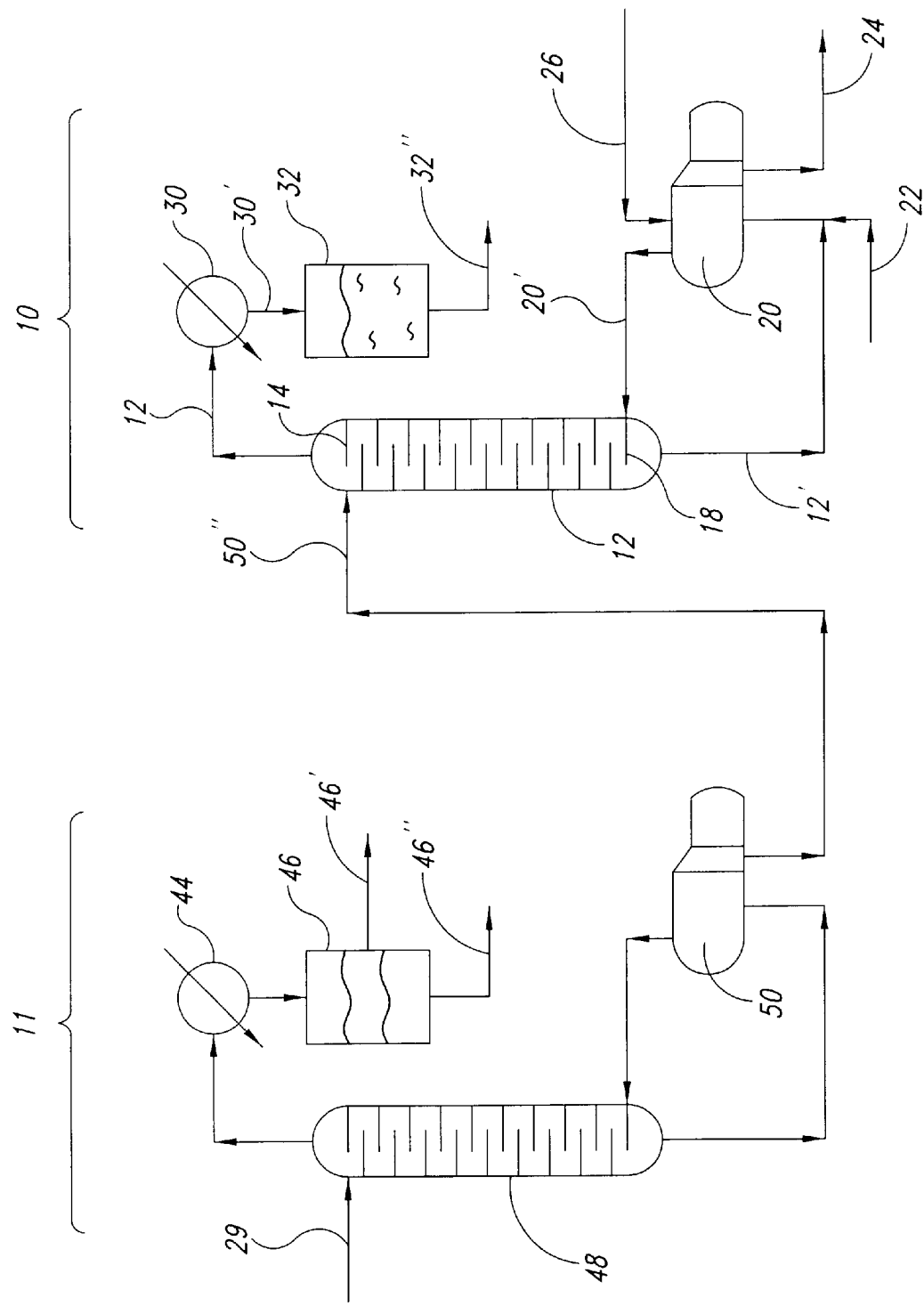
FIG. 4 illustrates a block diagram of another preferred embodiment of the present invention, which incorporates a pretreatment column.

A more efficient way to pre-treat the catalyst extract is to use a pre-treatment column 48 combined with a second re-boiler 50, better shown in FIG. 4, in place of the pre-flasher 40 of FIG. 3.

In the embodiment shown in FIG. 4, substantially all the cyclohexanone, with large amounts of water (⅔ of the water, for example) may be removed from the catalyst extract in the pre-treatment column, and form in the decanter 46 an upper liquid phase containing predominantly cyclohexanone (which is removed through line 46'), and a lower aqueous phase (which is removed through line 46"). In such a case, the pretreated catalyst extract will contain substantially no cyclohexanone, and therefore, there will be only a single liquid aqueous phase in the decanter 32, containing small amounts of acetic acid (around 1% by weight, for example). As in the embodiment of FIG. 3, if there is some acetic acid in the second extract line 29 (10–20% by weight, for example), it is preferable that lines 29 and 50" are connected to the vicinity of intermediate plates of the respective columns 48 and 12, respectively, thus forming an upper rectification section in addition to a lower stripping section.

It should be understood that according to the present invention, any liquids or gases or off-gases may be recycled totally or partially from any section to any other section, if so desired. Further, any combinations of the exemplifying embodiments, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers include artificially intelligent systems (expert systems, neural networks, and fuzzy logic systems, well known to the art). Of the three types of artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Regarding adipic acid, the preparation of which is especially suited to the methods of this invention, general information may be found in a plethora of U.S. Patents, among other references. These include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid) may be reacted, according to well known techniques to the art, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by techniques well known to the art to form fibers. The polymer may also be mixed with fillers and/or other additives to form composite materials.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All percentages are given by weight.

What is claimed is:

1. A method of replacing water and cyclohexanone with acetic acid in an aqueous solution of a metal catalyst, the solution having been produced after oxidation of cyclohexane to adipic acid, the method comprising steps of:

(a) feeding the aqueous solution of the metal catalyst to a top plate or an intermediate plate of a solvent exchange column, the solvent exchange column also having a bottom plate;

(b) removing a bottoms liquid from the vicinity of the bottom plate, the bottoms liquid being at a bottoms temperature;

(c) boiling the bottoms liquid in a re-boiler and returning produced bottoms vapors to the column in the vicinity of the bottom plate;

(d) introducing acetic acid to the re-boiler or to the vicinity of the bottom plate; and (e) removing from the re-boiler an acetic acid solution of the metal catalyst comprising no substantial amounts of water and cyclohexanone.

2. A method as defined in any of claim 1, further comprising a step of removing the majority of cyclohexanone and at least part of water before step (a).

3. A method as defined in claim 2, further comprising steps selected from a group consisting essentially of (a) forming a condensate on top of the solvent exchange column, and refluxing at least part of the condensate back to said solvent exchange column, (b) removing top vapors from the vicinity of the top plate of the solvent exchange column, condensing said vapors to form a condensate, and if the condensate constitutes two liquid phases, separating said condensate into an upper liquid phase comprising a majority of cyclohexanone, and a lower liquid phase comprising a majority of water, and (c) a combination thereof.

4. A method as defined in claim 3, further comprising a step of controlling and maintaining a parameter selected from a group consisting essentially of water content in the bottoms liquid, temperature at the bottoms liquid, and a combination thereof, within predetermined limits.

5. A method as defined in claim 4, wherein the metal catalyst comprises a cobalt compound.

6. A method as defined in claim 5, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

7. A method as defined in claim 3, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

8. A method as defined in claim 4, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

9. A method as defined in claim 2, further comprising a step of controlling and maintaining a parameter selected from a group consisting essentially of water content in the bottoms liquid, temperature at the bottoms liquid, and a combination thereof, within predetermined limits.

10. A method as defined in claim 9, wherein the metal catalyst comprises a cobalt compound.

11. A method as defined in claim 10, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

12. A method as defined in claim 9, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

13. A method as defined in claim 2, wherein the metal catalyst comprises a cobalt compound.

14. A method as defined in claim 13, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

15. A method as defined in claim 3, wherein the metal catalyst comprises a cobalt compound.

16. A method as defined in claim 15, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

17. A method as defined in claim 2, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

18. A method as defined in claim 1, further comprising steps selected from a group consisting essentially of (a) forming a condensate on top of the solvent exchange column, and refluxing at least part of the condensate back to said solvent exchange column, (b) removing top vapors from the vicinity of the top plate of the solvent exchange column, condensing said vapors to form a condensate, and if the condensate constitutes two liquid phases, separating said condensate into an upper liquid phase comprising a majority of cyclohexanone, and a lower liquid phase comprising a majority of water, and (c) a combination thereof.

19. A method as defined in claim 18, further comprising a step of controlling and maintaining a parameter selected from a group consisting essentially of water content in the bottoms liquid, temperature at the bottoms liquid, and a combination thereof, within predetermined limits.

20. A method as defined in claim 19, wherein the metal catalyst comprises a cobalt compound.

21. A method as defined in claim 20, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

22. A method as defined in claim 19, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

23. A method as defined in claim 18, wherein the metal catalyst comprises a cobalt compound.

24. A method as defined in claim 23, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

25. A method as defined in claim 18, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

26. A method as defined in claim 1, further comprising a step of controlling and maintaining a parameter selected from a group consisting essentially of water content in the bottoms liquid, temperature at the bottoms liquid, and a combination thereof, within predetermined limits.

27. A method as defined in claim 26, wherein the metal catalyst comprises a cobalt compound.

28. A method as defined in claim 27, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

29. A method as defined in claim 26, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

30. A method as defined in claim 1, wherein the metal catalyst comprises a cobalt compound.

31. A method as defined in claim 30, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

32. A method as defined in claim 1, further comprising a step of reacting the adipic acid with a reactant selected from a group consisting of a polyol, a polyamine, and a polyamide in a manner to form a polymer of a polyester, or a polyamide, or a (polyimide and/or polyamideimide), respectively, which method may also comprise steps of spinning the polymer into fibers or mixing the polymer with fillers and/or other additives to form composites.

\* \* \* \* \*

UNITED STATES PATENT AND TRADEMARK OFFICE
CERTIFICATE OF CORRECTION

PATENT NO. : 6,417,128 B1  Page 1 of 1
DATED : July 9, 2002
INVENTOR(S) : David C. DeCoster et al.

It is certified that error appears in the above-identified patent and that said Letters Patent is hereby corrected as shown below:

Title page,
Item [54], "METHODS AND REPLACING WATER AND CYCLOHEXANONE WITH ACETIC ACID IN AQUEOUS SOLUTIONS OF CATALYST" should read -- METHODS OF REPLACING WATER AND CYCLOHEXANONE WITH ACETIC ACID IN AQUEOUS SOLUTIONS OF CATALYST --
Item [73], Assignee, "RPC, Inc." should read -- RPC Inc. --
Item [57], ABSTRACT,
Line 14, "in a pretreatment zone" should read -- in a pre-treatment zone --

Signed and Sealed this

Twenty-ninth Day of July, 2003

JAMES E. ROGAN
*Director of the United States Patent and Trademark Office*